(12) United States Patent
Moldenhauer et al.

(10) Patent No.: US 6,861,447 B2
(45) Date of Patent: Mar. 1, 2005

(54) METHOD FOR PRODUCING A COENZYME Q10/γ-CYCLODEXTRIN COMPLEX

(75) Inventors: Jens Moldenhauer, Burghausen (DE); Jan Cully, Garching/Alz (DE)

(73) Assignee: Wacker-Chemie GmbH, Munich (DE)

(*) Notice: Subject to any disclaimer, the term of this patent is extended or adjusted under 35 U.S.C. 154(b) by 401 days.

(21) Appl. No.: 10/169,173

(22) PCT Filed: Jan. 11, 2001

(86) PCT No.: PCT/EP01/00305
§ 371 (c)(1),
(2), (4) Date: Jun. 27, 2002

(87) PCT Pub. No.: WO01/54730
PCT Pub. Date: Aug. 2, 2001

(65) Prior Publication Data
US 2003/0012774 A1 Jan. 16, 2003

(30) Foreign Application Priority Data
Jan. 27, 2000 (DE) .......................... 100 03 493

(51) Int. Cl.⁷ .............................................. A61K 31/35
(52) U.S. Cl. ...................... 514/460; 424/489; 424/94.1
(58) Field of Search ................ 424/489, 94.1; 514/460

(56) References Cited

FOREIGN PATENT DOCUMENTS

EP 0875240 A 11/1998

OTHER PUBLICATIONS

Motwani, M. Und Zatz, J.L., *"Applications of cyclodextrins in skin products"*, Cosmetics and Toiletries, vol. 112, No. 7, Jul. 1997 pp. 39–47, the whole document.

Loukas, Y. L. et al., *"Novel liposome–based multicomponent systems for the protection of photolabile agents"*, International Journal of Pharmaceutics, vol. 117, No. 1, 1995, pp. 85–94, XP 000986334, the whole document.

Matsubara, K. et al.: *"Controlled release of the LHRH agonist buserelin acetate from injectable suspensions containing triacetylated cyclodextrins in an oil vehicle"*, Journal of Controlled Release, vol. 31, No. 2, 1994, pp. 173–180, XP 000458317, the whole document.

Journal Acta Poloniae Pharmaceutica (1995) vol. 52, No. 5, pp. 379–386.

Journal Acta Poloniae Pharmaceutica (1996) vol. 53, No. 3, pp. 193–196.

*Primary Examiner*—Jean C. Witz
(74) *Attorney, Agent, or Firm*—Collard & Roe, P.C.

(57) ABSTRACT

A method is provided for producing a coenzyme Q10/γ-cyclodextrin complex. This method provides that a mixture of γ-cyclodextrin and coenzyme Q10 is treated by homogenisation and inputting energy.

10 Claims, No Drawings

METHOD FOR PRODUCING A COENZYME Q10/γ-CYCLODEXTRIN COMPLEX

CROSS REFERENCE TO RELATED APPLICATIONS

Applicant claims priority under 35 U.S.C. §119 of German Application No. 10003493.4 filed Jan. 27, 2000. Applicant also claims priority under 35 U.S.C. §120 of PCT/EP01/00305 filed Jan. 11, 2001. The international application under PCT article 21(2) was not published in English.

BACKGROUND OF THE INVENTION

1. Field of the Invention

The invention relates to a process for preparing a coenzyme Q10/γ-cyclodextrin complex.

2. The Prior Art

Cyclodextrins are cyclic oligosaccharides composed of 6, 7 or 8 α(1–4)-linked anhydroglucose units. The α-, β- or γ-cyclodextrins, which are prepared for example by enzymatic conversion of starch, differ in the diameter of their hydrophobic cavity and are generally suitable for inclusion of numerous lipophilic substances.

Coenzyme Q10 (ubiquinone) is an endocellular component which plays an important part in mitochondrial electron transport. Since it has been known that coenzyme Q10 improves the respiratory chain of the cell and strengthens the mitochondrial membrane, coenzyme Q10 has been employed for treating heart disease. Coenzyme Q10 also acts as free radical scavenger. It is also used for treating degenerative disorders. In addition, coenzyme Q10 improves the release of energy in the body. This property is utilized by the dietary supplement industry in the manufacture of products for sportsmen and for slimming. Coenzyme Q10 is moreover the active component in various cosmetic formulations.

Coenzyme Q10 is a lipid-soluble substance. It is a yellowish powder and is unstable in air. Its solubility in water is very poor. A formulation with γ-cyclodextrin is stable to air and light and increases the solubility in water and the bioavailability.

The complexation of coenzyme Q10 with various cyclodextrins and cyclodextrin derivatives using a kneading and a heating method is described in the *Journal Acta Poloniae Pharmaceutica* (1995), vol. 52, No. 5, pp. 379–386 and 1996, vol. 53, No. 3, pp. 193–196. The processes described therein for preparing a γ-cyclodextrin complex with coenzyme Q10 show various disadvantages on the production scale.

On use of the kneading method on the production scale, the dispersion necessary for complexation of the coenzyme Q10 is ensured only after agitation of the mixture for several hours. In the heating method, the material is kept at 333 K in a closed vessel for 164 hours. For economic reasons, therefore, these methods cannot be used to prepare a γ-cyclodextrin/coenzyme Q10 complex on the production scale.

SUMMARY OF THE INVENTION

It is an object of the invention to provide a process which does not have the disadvantages of the prior art and which makes it possible to prepare a γ-cyclodextrin/coenzyme Q10 complex in a rapid and uncomplicated manner.

The object is achieved by a process in which a mixture of γ-cyclodextrin and coenzyme Q10 is treated by homogenization and energy input.

An aqueous mixture of γ-cyclodextrin and coenzyme Q10 is preferably employed in the process of the invention.

The process starts, for example, from a concentrated aqueous γ-CD solution to which the coenzyme Q10 is added. However, it is equally possible first to prepare an aqueous coenzyme Q10 suspension and to add γ-CD thereto.

The mixture preferably contains a γ-CD concentration between 10–30% by weight. A CD concentration of 16–25% by weight is particularly preferred.

The coenzyme Q10 to γ-CD ratio by weight is preferably between 1:1 and 1:100, particularly preferably between 1:1 and 1:8, especially preferably between 1:1 and 1:6.

The homogenization is preferably effected using an Ultraturrax®, ultrasound apparatus, high-pressure homogenizer, ball mill or other equipment customary for homogenization.

The equipment advantageously used for effecting it simultaneously ensures energy input in the micro range. This is possible, for example, by means of equipment which generates ultrasound or a ball mill.

The energy input can be effected, for example, by heating the aqueous phase or the mixture of γ-cyclodextrin and coenzyme Q10 before or during the homogenization.

However, it is equally possible, and ordinarily adequate and preferred, to use only the heat likewise produced in the homogenization, such as, for example, the heat generated by the ultrasound or in the ball mill.

The energy input is therefore advantageously effected by equipment which simultaneously also brings about homogenization.

It has proved to be particularly advantageous to carry out the complexation in a ball mill because, in this case, there may also be, simultaneous with the micronization of the coenzyme Q10 particles, a local melting of these particles, with subsequent formation of the complexes with the dissolved γ-CD.

It is particularly preferred for homogenization and energy input to be effected simultaneously, for example through the use of a ball mill.

For example, the coenzyme Q10 and γ-CD/γ-CD solution is placed in a ball mill and mixed under nitrogen at 25° C. for from 10 to 60 min.

The kinetic energy of the beads further micronizes the coenzyme Q10 particles on impact. Part of this energy is converted into heat, which causes local melting of the Q10 particles present in the microenvironment. These are then complexed by the surrounding CD.

The process of the invention preferably takes place in a temperature range of 10–80° C.

It is particularly preferably carried out at 15–40° C., especially preferably at about 25° C.

The duration of the homogenization depends on the temperature, the stirring speed and the geometry of the ball mill. A mixing time of from 1 to 60 min is ordinarily adequate.

The complexation ordinarily takes place under atmospheric pressure. This does not, of course, apply when the process is carried out with use of equipment (for example a high-pressure emulsifier) which is normally used under different pressure conditions. The pressure conditions normal for the particular equipment are employed when such equipment is employed for the process.

The complexation preferably takes place under a protective gas atmosphere (nitrogen or argon).

The complexes can be used directly in the form of the reaction mixture.

However, they are preferably isolated by filtration, centrifugation, drying, grinding, screening, sifting, granulating, tableting appropriate for the procedure usual in each case, and processed to give a stable powder. Thus, the coenzyme Q10/γ-CD complex can be dried for example in a drying oven at 55° C. for 12 hours, and the drying can be followed by a grinding.

DETAILED DESCRIPTION OF PREFERRED EMBODIMENTS

The following examples serve to illustrate the invention further.

EXAMPLE 1

18 g of γ-CD (can be purchased under the name Cavamax® from Wacker Chemie, Munich) were added to 72 ml of water in a Netzsch PE 75 ball mill with zirconium oxide milling elements of d 0.4 mm and resuspended at 1000 rpm and room temperature for 30 seconds. Then 4.5 g of coenzyme Q10 powder (obtainable from Eurotech GmbH) were added, and mixing was continued at room temperature and 1200 rpm for 15 minutes. After removal of the zirconium oxide milling elements with a sieve, the material was dried in a drying oven at 55° C. The white powder obtained in this way with a water content of about 6% contains 22% coenzyme Q10.

EXAMPLE 2

15 g of γ-CD were dissolved in 75 ml of water at 70° C. 3 g of coenzyme Q10 in 6 ml of diethyl ether were added to the solution, and then homogenization was carried out in an IKA® Ultraturrax® T50 at 10,000 rpm for 30 seconds. The mixture was cooled on a magnetic stirrer to room temperature within 30 minutes. The material was then dried in a drying oven at 55° C. The white powder obtained in this way with a water content of about 6% contains 20% coenzyme Q10.

EXAMPLE 3

6 g of coenzyme Q10 were homogenized in 60 ml of water in an Ultraturrax at 70° C. 80 ml of an aqueous solution containing 26 g of γ-CD at 70° C. were added to the homogenate. The mixture was then homogenized with an IKA® Ultraturrax® T50 at 10,000 rpm for 30 seconds. The mixture was cooled by stirring on a magnetic stirrer to room temperature within 30 minutes. The material was then dried in a drying oven at 55° C. The white powder with a water content of about 6% contains 25% coenzyme Q10.

What is claimed is:

1. A process for preparing a γ-cyclodextrin (γ-CD)/coenzyme Q10 complex comprising preparing a mixture of γ-cyclodextrin and coenzyme Q10; and treating said mixture by homogenizing and inputting energy by means of heating or ultrasound.

2. The process as claimed in claim 1, comprising employing an aqueous mixture of γ-cyclodextrin and coenzyme Q10.

3. A process as claimed in claim 1, wherein γ-CD concentration in the mixture is between 10–30% by weight based upon the total weight of the mixture.

4. The process as claimed in claim 1, wherein the weight ratio of coenzyme Q10 to γ-CD is between 1:1 and 1:100.

5. The process as claimed in claim 1, wherein the homogenizing is effected by an apparatus selected from the group consisting of ultrasound apparatus, ball mill, Ultraturrax® and high-pressure homogenizer.

6. The process as claimed in claim 1, wherein the inputting of energy is effected by heating the mixture of γ-cyclodextrin and coenzyme Q10 in a manner selected from the group consisting of before homogenizing and during homogenizing.

7. The process as claimed in claim 1, wherein the inputting of energy is effected by heating equipment which simultaneously also bring about the homogenizing.

8. The process as claimed in claim 7, wherein homogenizing and inputting of energy are effected simultaneously through use of a ball mill.

9. The process as claimed in claim 8, comprising carrying out the homogenizing in a temperature range from 10 to 80° C.

10. The process as claimed in 1, wherein the process takes between 1 and 60 min.

\* \* \* \* \*